(12) United States Patent
Leight

(10) Patent No.: US 6,345,684 B1
(45) Date of Patent: Feb. 12, 2002

(54) CHECKABLE EARPLUG

(75) Inventor: Howard S. Leight, Malibu, CA (US)

(73) Assignee: Bacou USA Safety, Inc., San Diego, CA (US)

( * ) Notice: Subject to any disclaimer, the term of this patent is extended or adjusted under 35 U.S.C. 154(b) by 0 days.

(21) Appl. No.: 09/568,870

(22) Filed: May 9, 2000

Related U.S. Application Data

(63) Continuation-in-part of application No. 09/104,802, filed on Jun. 25, 1998, now abandoned, which is a continuation of application No. 08/944,094, filed on Oct. 2, 1997, now Pat. No. 5,811,742.
(60) Provisional application No. 60/043,733, filed on Apr. 21, 1997.

(51) Int. Cl.$^7$ .............................. A61B 7/02; A61F 11/00
(52) U.S. Cl. ......................................... 181/135; 128/864
(58) Field of Search .................. 181/135, 130; 128/857, 864–868

(56) References Cited

U.S. PATENT DOCUMENTS

| | | | | |
|---|---|---|---|---|
| 4,384,575 A | * | 5/1983 | Asker | 128/864 |
| 5,573,015 A | * | 11/1996 | Williams | 128/864 |
| 5,727,566 A | * | 3/1998 | Leight | 128/857 |
| 5,811,742 A | * | 9/1998 | Leight | 181/135 |
| 5,957,136 A | * | 9/1999 | Magidson et al. | 128/864 |
| 6,105,715 A | | 8/2000 | Knauer | |

* cited by examiner

Primary Examiner—Khanh Dang
(74) Attorney, Agent, or Firm—Leon D. Rosen

(57) ABSTRACT

An earplug has a front portion (14) for entering the ear canal and a rear portion (16) that serves as a handle, with a marking (56) near their intersection to indicate to a supervisor whether or not the earplug has been fully installed. The marking is preferably the result of the front and rear portions being formed of material of different colors. Thus, if a supervisor observes a location where a color change occurs, at a significant distance out of the worker's ear canal, the supervisor is informed of a possible insufficient depth of earplug installation.

8 Claims, 2 Drawing Sheets

CHECKABLE EARPLUG

CROSS REFERENCE TO RELATED APPLICATIONS

This is a continuation-in-part of U.S. patent application Ser. No. 09/104,802 filed Jun. 25, 1998, now abandoned, which is a continuation of U.S. patent application Ser. No. 08/944,094 filed Oct. 2, 1997 and now U.S. Pat. No. 5,811,742 issued Sep. 22, 1998 which claimed the benefit of U.S. provisional patent application 60/043,733 filed Apr. 21, 1997.

BACKGROUND OF THE INVENTION

Earplugs are used to protect a worker's hearing in a noisy environment. Such earplugs commonly have a front portion for tightly fitting in a person's ear canal to block noise, and a rear portion that serves as a handle to pull out the earplug from the ear canal. Probably the most common type of earplug in current use is a body of molded slow recovery foam polymer whose front portion is rolled between the fingers to a small diameter, inserted into the ear canal, and allowed to expand while it lies within the ear canal. Such earplugs and other types, must be inserted to a minimum depth in order to effectively block the ear canal. Many persons are leary of inserting objects in their ears, and tend to insert the earplugs less than the minimum amount required for highest noise blocking. Such workers are often not aware of the fact that the earplug has been insufficiently inserted, because the earplug is often inserted far enough to considerably reduce the noise, although not far enough to avoid hearing damage over a long period of time where very loud noises are encountered. Supervisors are responsible for assuring that the workers' hearing is protected. However, supervisors often cannot determine whether or not the earplug has been sufficiently inserted to obtain full benefit of the noise blocking capability of the earplug. An earplug which readily indicated to a supervisor that it might not be sufficiently inserted to protect the worker's hearing, would be of value.

SUMMARY OF THE INVENTION

In accordance with one embodiment of the present invention, an earplug is provided which aids a supervisor in determining whether or not the earplug is likely to have been fully installed in a worker's ear canal so as to obtain substantially optimum hearing protection. The earplug has front and rear portions, with the front portion constructed to fit into a person's ear canal and block noise, and with the rear portion forming a handle for pulling out the front portion from the ear canal. The earplug has a marking at the rear end of the front portion, to provide a visual indication that the front portion has not been fully inserted. If a supervisor notices the marking, then the supervisor has noticed that the earplug has not been fully installed. In some cases, effective blocking is achieved with slightly less than full installation, and a supervisor can note that the marking projects only a small distance out of the ear canal and realizes that the earplug has been installed to a sufficient depth.

The marking is preferably a result of the front and rear portions of the earplug being formed of material of different colors. This can be achieved by molding the front and rear portions of substantially the same material, but with different coloring agents that create different colors, and bonding the front and rear portions together. Thus, if a supervisor observes a location where a color change occurs, where the location is a sufficient distance out of the ear canal to indicate a problem, the supervisor is informed of the problem. The problem of insufficient insertion can be especially common where there is a taper along the front portion of the earplug.

In accordance with one embodiment of the invention, The novel features of the invention are set forth with particularity in the appended claims. The invention will be best understood from the following description when read in conjunction with the accompanying drawings.

DESCRIPTION OF THE PREFERRED EMBODIMENTS

Figure 1:
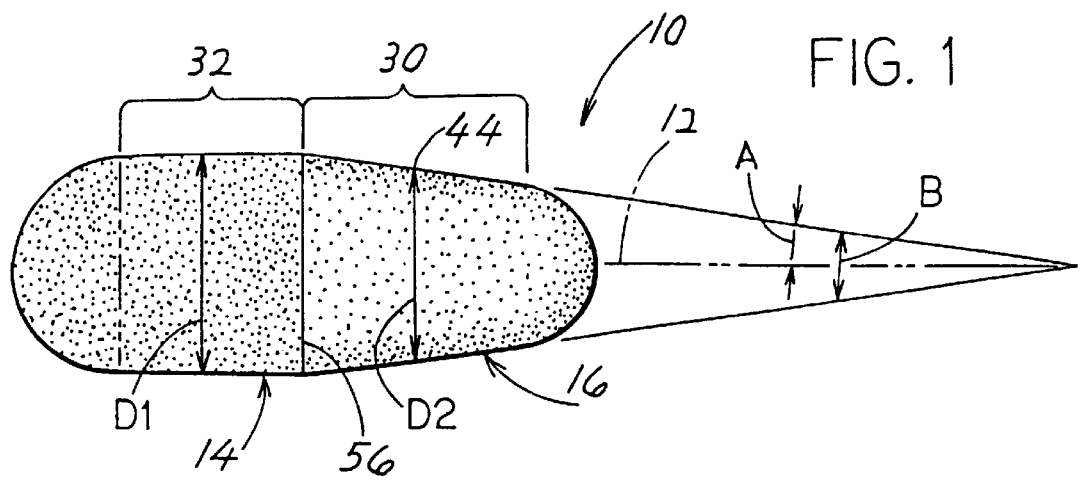
FIG. 1 is a side elevation view of an earplug constructed in accordance with one embodiment of the invention.
Figure 2:
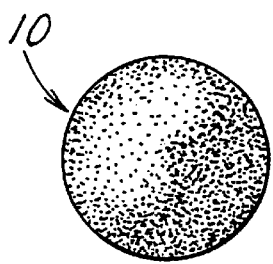
FIG. 2 is a left side view of the earplug of FIG. 1.

FIG. 1 illustrates an earplug 10 that is elongated along an axis 12 and symmetrical about the axis. The earplug, or earplug body, has first and second opposite end portions 14, 16 that are each designed to lie in an interference fit in an ear canal to block the passage of noise through the ear canal. The first end portion has a large diameter D1 at a location where it is designed to lie in an ear canal, while the second end portion has a smaller diameter D2 at a location that is designed to lie at the entrance of a small ear canal. The earplug is substantially filled with slow recovery foam material, and is intended to protect the hearing of workers who work in a noisy environment.

Figure 4:
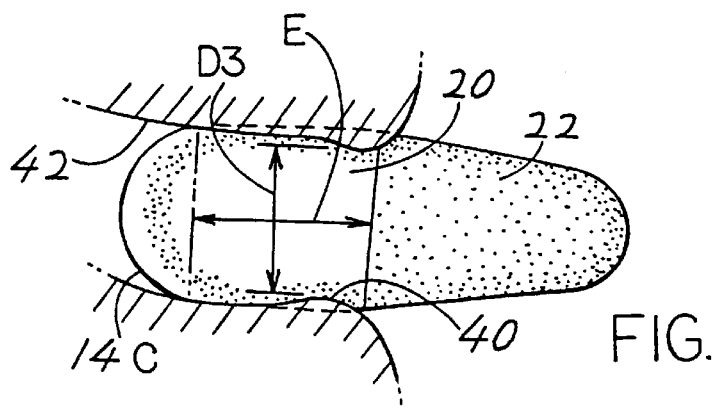
FIG. 4 is a side elevation view of the earplug of FIG. 1, showing the larger end fully installed in a larger ear canal.
Figure 5:
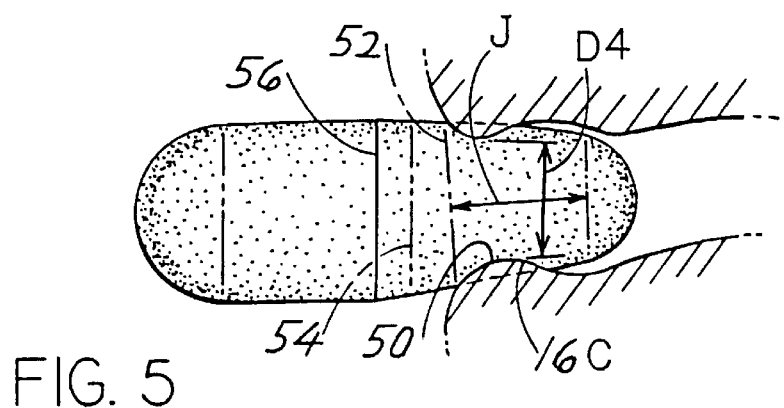
FIG. 5 is a side elevation view of the earplug of FIG. 1, showing the smaller end partially installed in a smaller ear canal.

The second or smaller end portion 16 (FIG. 1) of the earplug is tapered along its entire length, with the tapering along the length 30 which is most of the length and actually all of it except for the small end, being at a constant taper angle A of about 7½° from the axis 12 and forming an included angle B of 15°. For a medium to high friction material such as a molded slow recovery foam, the friction of the earplug surface with the ear canal avoids the earplug working its way out of the ear canal for a small taper angle B of about 15° (7.5° to 22.5°). The large end portion 14 is cylindrical at a part 32 that is about half of the length of the end portion 16. The presence of the cylinder at 32 helps to visually distinguish the large end from the small end which is tapered along its entire length. The tapering of the small end portion 16 results in it merging with the cylinder at 32, which avoids steps. FIGS. 4 and 5 show the opposite end portions of the earplug installed into ear canals of different sizes. In FIG. 4, the large end 14C of the earplug is shown having been installed through the entrance 40 to a large ear canal 42. The larger earplug end portion 14 has an uncompressed diameter D1 of about 0.43 inch, while the larger-than-usual entrance 40 to the particular person's ear canal shown in FIG. 4, has a diameter D3 of 0.33 inch. As a result, the large diameter end portion at 14C is compressed by about 24% at the entrance 40 and somewhat less at larger diameter portions of the ear canal.

The small diameter end 16 (FIG. 1) of the earplug has a diameter D2 of about 0.37 inch at a location 44 halfway along its region 30 of constant taper. It is noted that the entrance to the ear canal is often non-circular so only slight earplug compression can leave a gap.

In FIG. 5, the entrance 50 to the small ear canal has a diameter D4 of about 0.27 inch. This results in the small diameter earplug end portion at the location 44 being compressed to the configuration 16C wherein it is compressed by about 27% at the entrance to the ear canal. Such compression is generally effective and comfortable. If the large diameter end portion 14 of the earplug were inserted into the smaller ear canal, then at the entrance 50, the compression of the earplug would be 37%, which is likely to be uncomfortable to the person who has a smaller diameter ear canal.

Figure 3:
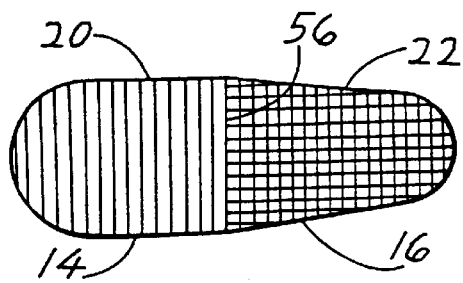
FIG. 3 is a view similar to that of FIG. 1, but with the colors of the opposite portions of the earplug being shown by cross hatching.

FIG. 3 shows the earplug of FIG. 1, but with cross hatch lines showing the different colors 20, 22 of the different end portions 14, 16. The different colors allow a person to determine which end of the earplug is the larger one, at a glance and even in poor lighting conditions. In FIG. 3, the color 20 of the larger end portion is red, while the color 22 of the second end portion is yellow. The different colors not only help determine which end is larger, but also aid a supervisor or other person, to determine whether or not the depth of insertion of the earplug into the ear canal is sufficient to protect the worker's hearing.

Where an earplug front portion is of substantially constant diameter (and includes a taper angle of no more than about 5°) effective noise blocking is generally obtained when the depth of insertion E (FIG. 4) is at least about 75% of the initial earplug diameter (D1). The depth of insertion E should be at least 60% of the initial diameter (D1) to obtain close to optimum noise blocking, and is preferably no more than 120% of initial diameter to avoid wastage of material. In FIG. 4, such full insertion can be noted by a supervisor who views the outside of the worker's ear canal, because no part of the large diameter portion of the earplug, which is of red color, can be seen by the supervisor. Even if the supervisor should see a small band of red projecting from the worker's ear canal, the supervisor would know that the earplug is fully inserted, and that further insertion will not increase hearing protection. It is noted that the insertion distance E in FIG. 4 is slightly greater than necessary.

For the tapered earplug end of FIG. 5, the minimum insertion required for maximum hearing protection varies with the size of the ear canal of the worker. If the worker has a small ear canal, then maximum hearing protection will be obtained with only a small depth of insertion J, where the line 52 represents the location where any portion of the earplug lying outside that location can be seen by a supervisor. Where a person has a somewhat larger ear canal, the earplug should be inserted to a greater depth, as where a line 54 lies at the entrance to the ear canal. A supervisor viewing the worker preferably has tested the worker to determine whether an insertion to the line 54 is more effective than an insertion to the line 52, or whether an insertion to the line 56 is more effective. The supervisor can then note that for that worker a slight or moderate ring of yellow color that can be observed from looking at the ear canal, indicates sufficient earplug insertion. A larger band of yellow color would indicate that the earplug is not inserted sufficiently deep.

Figure 6:
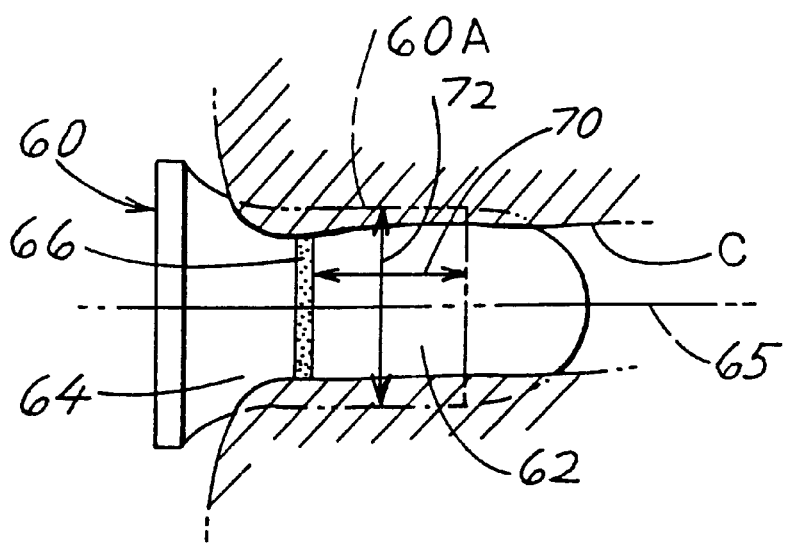
FIG. 6 is a side elevation view of an earplug constructed in accordance with another embodiment of the invention.

FIG. 6 shows another earplug 60 which is constructed of slow recovery foam material which is molded to the shape 60A. The earplug has front and rear portions 62, 64, spaced along an axis 65 and having substantially circular cross-sections along the axis. The earplug front portion 62 is designed to fit in the ear canal C and the rear portion serves as a handle to aid in insertion of the earplug and in its withdrawal or pullout from the ear canal. Applicant may form the front and rear portions 62, 64 of material of the same color, with a marking at 66 at the intersection of these portions. The marking 66 is a band having an axial length less than its diameter. Marking 66 is formed from material of a different color from at least the rear portion 64. In one example, the mark at 66 is a section of the earplug formed of red material, while the front and rear portions 62, 64 are both formed of yellow colored material. The earplug could have three or more different colors, such as with two or more bands 66 of different colors. Although applicant prefers that the earplug be installed as illustrated in FIG. 6, it usually provides substantially maximum sound sealing when at least the mark 66 lies within the ear canal. Then, a length 70 of about 75% of the original diameter 72 lies within the ear and will effectively block noise. However, if a supervisor sees the mark 66 protruding or protruding more than a small amount from the ear canal, the supervisor is informed that the earplug has not been sufficiently installed. If a slight strip of the yellow front portion 62 is showing, then the width of that yellow strip indicates the degree of insufficient depth of insertion.

Although the construction of FIG. 6 can be used, it can add to cost where three separate sections 62, 64, 66 must be separately molded and bonded (as by pressing them together while the material is hot). It is possible to apply ink to the location 66 of an earplug molded in a single piece, but applicant has not tried this.

Figure 7:
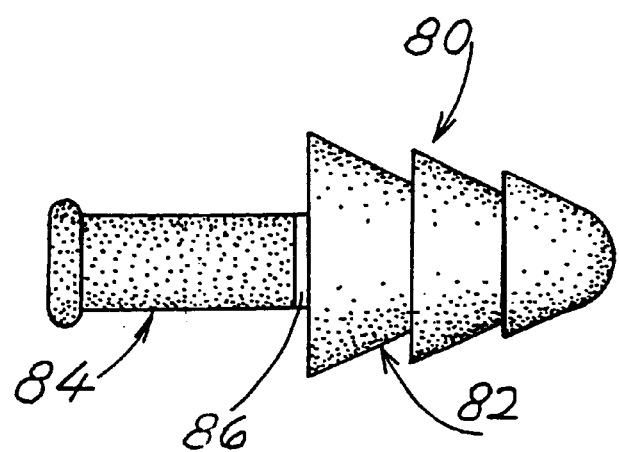
FIG. 7 is a side elevation view of an earplug constructed in accordance with another embodiment of the invention.

FIG. 7 illustrates another earplug 80 which includes a solid rubber-like material. A front portion 82 has three thin flanges of progressively smaller initial diameters at progressively more forward locations. The earplug should be installed with all three flanges lying within the ear canal. The front portion 82 is molded of a material of particular color such as yellow. A rear portion 84 of the earplug, which is also of rubber-like material, is of a different color, such as brown. The rear portion 84 is used to insert the front portion into the ear canal and withdraw it. The earplug is preferably inserted so the rear end 86 of the front portion lies within the ear canal. If a supervisor sees the yellow color of the front portion 82, then the supervisor is informed that the earplug is not fully inserted. It may be that the rear end 86 projects slightly from the ear canal, in which case the earplug is probably highly effective. However, if the rear end 86 projects by more than a few millimeters from the ear canal, then the supervisor who sees this can note that the earplug probably has to be inserted deeper.

Thus, the invention provides an earplug that enables a supervisor, coworker, or the wearer who looks in a mirror, to determine whether or not the earplug has been sufficiently (fully) inserted into that person's ear canal to obtain substantially maximum hearing protection (within about 3 db of maximum, which may be about 28 db). The earplug has front and rear portions, with the front portion constructed to fit into the ear canal to block noise, and with the rear portion forming a handle to aid in pushing in or pulling out the front portion from the ear canal. The earplug has a marking at the rear end of the front portion, to provide a visual indication that the front portion has not been fully inserted into the ear canal. The marking is preferably formed by an intersection of 2 different colors. This is preferably achieved by forming the front and rear portions of elastomeric material such as a slow recovery foam, which have different coloring agents, so the earplug has different colors at its front and rear portions. The marking is preferably placed at a location where it begins to project (more than perhaps 2 mm) from the earplug only when there is insufficient insertion to create a reasonable possibility that the workers' ears are not fully protected from noise. The marking can be formed by a band of a color different from colors forward or rearward of the band. For earplugs of solid foam material having a section of largely cylindrical shape for fitting into the ear canal, the length of the cylindrical section that fits into the ear canal should be at least about ¾ of the diameter of the section and the marking is placed at the rear end of about this length of the cylinder.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug wherein:
    said earplug has front and rear portions, with said front portion constructed to fit into an ear canal and block noise, and with said rear portion forming a handle for pulling out the front portion from the ear canal;
    said earplug has a marking at the rear end of said front portion, to provide a visual indication that the front portion has not been fully inserted into the ear canal.
2. The earplug described in claim 1 wherein:
    said front and rear portions are of first and second different colors, respectively, with said marking formed by said first color at said rear end of said first portion, so that a display of said first color outside the ear canal indicates less than full insertion of said earplug.
3. The earplug described in claim 1 wherein:
    said front and rear portions are formed from different quantities of substantially the same material except that said front and rear portions contain coloring agents that display different colors, with said different quantities being bonded together.
4. An earplug comprising:
    an earplug body having front and rear portions that are of different first and second colors, with the length of said front portion of said earplug being about the minimum length of insertion of said body into a person's ear canal which assures effective noise blocking, so a supervisor who observes said first color at the person's ear is alerted to possible insufficient installation of the earplug.
5. The earplug described in claim 4 wherein:
    said front and rear earplug portions are each constructed of substantially the same resilient foam material, but they have different coloring agents in their chemical compositions.
6. An earplug wherein:
    said earplug is formed of foam material which has a substantially cylindrical front portion for insertion in an ear canal and a rear portion for projecting out of said ear canal, with said substantially cylindrical front portion having a length of between 60% and 120% of its initial diameter, and with said front and rear portions being of distinctly different colors.
7. A method for assuring that a person is safeguarded from hearing injury in a noisy environment, comprising:
    inserting front portions of earplugs into the person's ears, where the earplugs have markings at the rear ends of said front portions;
    viewing said person to observe whether or not said markings are visible and to observe the observable lengths of any visible portions of said markings, to thereby determine the likelihood of insufficient installation.
8. The method described in claim 7 wherein:
    said earplugs have rear portions of a second color, and said front portions are of a first color which is different from said second color, with the intersection of said first and second colors forming said markings;
    said step of viewing includes looking for said first color along the areas of said earplugs that are visible.

* * * * *